United States Patent [19]

Jung et al.

[11] Patent Number: 5,478,576
[45] Date of Patent: Dec. 26, 1995

[54] ARABINOGALACTAN DERIVATIVES AND USES THEREOF

[75] Inventors: Chu Jung, Arlington; Philip Enriquez, Sheldonville; Stephen Palmacci, Walpole; Lee Josephson, Arlington; Jerome M. Lewis, Newton, all of Mass.

[73] Assignee: Advanced Magnetics, Inc., Cambridge, Mass.

[21] Appl. No.: 900,686

[22] Filed: Jun. 17, 1992

Related U.S. Application Data

[63] Continuation-in-part of Ser. No. 630,017, Dec. 19, 1990, abandoned, which is a continuation-in-part of Ser. No. 384,991, Jul. 28, 1989, abandoned, which is a continuation-in-part of Ser. No. 228,640, Aug. 4, 1988, abandoned, which is a continuation-in-part of Ser. No. 67,586, Jun. 26, 1987, Pat. No. 4,827,945, which is a continuation-in-part of Ser. No. 882,044, Jul. 3, 1986, Pat. No. 4,770,183.

[51] Int. Cl.$^6$ ............................ C07K 17/00; A61K 38/14
[52] U.S. Cl. ............................ 424/488; 530/345; 530/813; 536/1.11; 536/4.1; 536/123.1; 536/103; 536/112; 514/54; 135/178
[58] Field of Search ..................... 530/345, 813; 536/1.1, 4.1; 424/488; 514/54; 435/178

[56] References Cited

U.S. PATENT DOCUMENTS 5,041,541  8/1991  Mazur ........................................ 536/11

*Primary Examiner*—Jill Warden
*Assistant Examiner*—Carol Salata
*Attorney, Agent, or Firm*—Bromberg & Sunstein

[57] ABSTRACT

A substantially purified arabinogalactan, its degradative products and selected modifications thereof have been found to act as carriers for delivering therapeutic agent to cell receptors capable of receptor mediated endocytosis (RME). The arabinogalactan and its degrative products once derivatived are capable of forming a complex between the therapeutic agent and the polysaccharide such that the complex retains the ability to recognize and bind to the RME receptor.

6 Claims, No Drawings

ARABINOGALACTAN DERIVATIVES AND USES THEREOF

CROSS REFERENCE TO RELATED APPLICATIONS

This application is a continuation in part of U.S. Ser. No. 07/630,017, filed Dec. 19, 1990, now abandoned which is continuation-in-part of U.S application Ser. No. 07/384,991 filed Jul. 28, 1989 now abandoned, which is a continuation-in-part of U.S. application Ser. No. 07/228,640 filed Aug. 4, 1988 now abandoned, which is a continuation-in-part of U.S. application Ser. No 067,586 filed Jun. 26, 1987, now U.S. Pat. No. 4,827,945, which in turn is a continuation-in-part of U.S. application Ser. No. 882,044, filed Jul. 3, 1986, now U.S. Pat. No. 4,770,183.

TECHNICAL FIELD

This invention relates to the synthesis and methods of use of therapeutic agents targeted to cells, especially hepatocytes.

BACKGROUND ART

The safety and efficacy of a therapeutic agent is a function of (i) its intrinsic biological activity and (ii) the biodistribution achieved after its administration. Many potentially useful therapeutic agents possess a biochemical activity ameliorating a particular pathological condition, but the presence of the agent in normal, nonpathological tissue results in deleterious effects that prevent the use of the agent. Damage to a normally functioning kidney, bone marrow, liver tissue or other organ may limit the use of therapeutic agents with established antiviral activity, or agents with established anti-cancer activity. There is a need for new compounds to target therapeutic agents to the specific cells that are the source of some pathological condition, and to reduce the concentration attained in unaffected, normal tissues. Targeting is the modification of a therapeutic agent so that after injection or oral administration the uptake by a specific population of cells is increased relative to uptake of the unmodified agent. By targeting compounds with established and beneficial biological activity to specific tissues, compounds whose use is currently limited by side effects might become safe and efficacious drugs. A therapeutic agent is a compound administered with the intent of changing in a beneficial manner some physiological function. Therapeutic agents include radioprotective agents, chemoprotective agents, antiviral agents, antibodies, enzymes, and peptides.

One method of targeting therapeutic agents to specific cells involves attaching them to carrier molecules recognized by receptors performing receptor mediated endocytosis. Of particular interest is targeting via the asialoglycoprotein receptor of hepatocytes. This receptor is present in high levels on normal hepatocytes but in lower levels or not at all on transformed hepatocytes (hepatoma cells). Diagnostic and therapeutic agents have been attached to asialoglycoprotein carriers and neoglycoprotein carriers recognized by the asialoglycoprotein receptor and targeted to the cells, see Table II of Meijer and van der Sullies, Pharm. Res. (1989) 6:105–118 and Ranade, J. Clin. Pharmacol. (1989) 29:685–694. Molecules recognizing the asialoglycoprotein receptor are most often either asialoglycoproteins or neoglycoproteins. Asialoglycoproteins are formed by removing the sialic acid of glycoproteins and exposing galactose residues. Neoglycoproteins are formed by attaching multiple galactose residues to non-glycoproteins such as human albumin.

When attaching diagnostic and therapeutic agents to a receptor-recognizing carrier molecule, targeting can be achieved only if the affinity of the carrier for the receptor is maintained. The differential reactivity of the protein amine and carbohydrate hydroxyl groups of glycoprotein carriers, e.g. asialofetuin, is commonly used to achieve this goal. The highly reactive amine groups of protein lysine residues are selectively modified, while the hydroxyl groups of carbohydrate are left intact and continue to recognize the receptor. Examples of this strategy are given in Van der Sluijs et al. (above) and in "Liver Diseases, Targeted Diagnosis and Therapy Using Specific Receptors and Ligands" (1991) Ed. G. Y. Wu and C. H. Wu, Marcel Dekker Inc. pp. 235–264. In contrast, a polysaccharide such as arabinogalactan offers no polypeptide amino groups distal from the receptor binding site that can be modified for the purposes of retaining the asialoglucoprotein receptor binding activity. In spite of the obvious strategy for modification of glycoproteins with retention of receptor binding activity, their use for targeted, parenteral pharmaceuticals is subject to several problems.

(i) Glycoproteins are prepared from animal cells and insuring noncontamination with human infective viral pathogens is a major issue.

(ii) Glycoproteins will not generally tolerate organic solvents during conjugate synthesis, because such solvents frequently lead to a loss of biological activity and denaturation.

(iii) Glycoproteins can be toxic and/or antigenic.

(iv) Glycoproteins in their native form, e.g. fetuin, do not afford galactose resides and must be desialylated to produce a carrier which interacts with the receptor.

Arabinogalactans are a class of polysaccharides obtained from the cell walls of many species of trees and other plants. A common, commercially available source of arabinogalactan is the American Western larch (*Larix occidentalis*). Arabinogalactan from this source is used as a binder, emulsifier or stabilizer in foods. It consists of a largely 1–3 linked D-galactose backbone with 1–6 linked branch chains of L-arabinoses and D-galactoses at practically every residue on the backbone. In larch arabinogalactans the ratio of galactose to arabinose is between 5 to 1 and 10 to 1, while arabinogalactans from plant sources in general range from about 1 to 4 to about 10 to 1 [Clarke, A. E., Anderson, R. L., Stone, B. A.; Phytochemistry (1979) 18: 521–40]. Like many polysaccharides, arabinogalactans have different molecular weights with values of about 1–2 million to about 10,000 daltons [Blake, J. D., Clarke, M. L., Jansson, P. E.; Carbohydr Res (1983) 115: 265–272] having been reported. It has been shown that L-arabinose and D-galactose interact with the asialoglycoprotein receptor while common monosaccharides like glucose or mannose do not [Lee, Haekyung, Kelm, Sorge, Teruo, Yoshino, Schauer, Roland Biol. Chem., Hoppe-Seyler (1988) 369, 705–714].

Some derivatives of arabinogalactan have been previously prepared. Graft copolymers have been used in paper manufacturing [SU1285094] and in soil treatments [JP1051198]. Arabinogalactan sulfate has been used to form salts with drugs to influence drug absorption and prolong drug action [US4609640]. Acidic forms of arabinogalactan occur naturally having a composition which includes uranic acid [Clarke, A. E., Anderson, R. L., Stone, B. A., Phytochemistry (1979) 18, 521–40], and have also been prepared from arabinogalactan [JP60219202]. Derivatives of arabinogalactan with substituent alkyl, allyl cyano, halo or amino groups, and conjugates with organic acids and enzyme protein have been disclosed, wherein the carbohydrate is used as a carrier, adsorbent or resin [JP60219201]. In some cases arabinogalactan has been highly derivatized in a manner likely to destroy its interaction with the asialoglycoprotein receptor. For example, in some cases as many as 50% of the hydroxyl groups of arabinogalactan have been modified [JP60219201], but the affinity, or lack thereof, of arabinogalactan derivatives for the asialoglycoprotein receptor has not been studied.

SUMMARY OF INVENTION

The present invention provides for derivatives of arabinogalactan which can be used to target therapeutic agents to the cells possessing the asialoglycoprotein receptor.

The use of the polysaccharide arabinogalactan to target therapeutic agents to cells via the asialoglycoprotein receptor, a feature of the current invention, overcomes problems encountered when glycoproteins are used for this purpose.

(i) A polysaccharide like arabinogalactan originating from a plant source is unlikely to be contaminated with human viral pathogens.

(ii) Since arabinogalactan is a polysaccharide, it will tolerate exposure to organic solvents, which normally denature proteins during conjugate synthesis. Composed exclusively of sugars, the polysaccharide presents a narrow spectrum of reactive sites, an advantage compared to proteins where the variety of reactive sites can lead to unwanted synthetic byproducts. This advantage is evident in the examples below.

(iii) Arabinogalactan has low toxicity and antigenicity.

(iv) Arabinogalactan in its natural form reacts with the asialoglycoprotein receptor. This helps reduce manufacturing cost because the deasialylation reaction normally used to expose the penultimate galactose of glycoproteins is avoided.

We have discovered that arabinogalactan can be modified in a number of ways to produce molecules which preserve the useful affinity for the asialoglycoprotein receptor. This is surprising since arabinogalactan does not afford protein or amino groups for selective modifications distal from the receptor binding site. The ability to modify arabinogalactan while retaining its biological activity permits its use as a carrier for a wide variety of therapeutic agents with various targeting strategies.

In some instances targeting may be employed to deliver a therapeutic agent to normal rather than pathological tissue. This strategy is employed when it is desirable to protect normal tissues from other generally toxic agents; in some cases agents of known but controlled toxicity are employed in therapy. The targeting of protective agents used in conjunction with normally toxic radiation, as in radiation therapy, is an embodiment of the current invention and example of this type of targeting. The targeting of protective agents used with chemotherapeutic agents used in cancer treatment is another embodiment of the current invention. The use of the term "therapeutic agent" in this description and the accompanying claims, includes agents which are protective from toxic chemicals or radiation.

The arabinogalactan derivatives of the invention must interact strongly with the asialoglycoprotein receptor, so they can be used to target therapeutic agents to cells via that receptor. An assay to determine the strength of the interaction of arabinogalactan derivatives of the invention with the receptor is presented.

In one embodiment the antiviral therapeutic agent adenosine arabinoside mono-5'-phosphate (ARA-AMP) is coupled to arabinogalactan. In addition, ARA-A of acyclovir, both antiviral therapeutic agents, may also separately be coupled to arabino-galactans. In another embodiment the radioprotective agent S-2-(3 aminopropylamino) ethylthiophosphoric acid (known as WR2721) is attached to arabinogalactan. The invention provides methods and compositions which enable the attachment of a variety of therapeutic agents to arabinogalactan and the delivery of those agents into the cytoplasm of cells via endocytotic activity of the asialoglycoprotein receptor.

DETAILED DESCRIPTION OF SPECIFIC EMBODIMENTS

The arabinogalactan used here in a preferred embodiment is highly purified and substantially free of endotoxins, and is derived from the Western Larch and has a single peak by size exclusion chromatography of about 20,000 daltons. Arabinogalactan can be used in its native, 20,000 dalton form; alternatively polymers of arabinogalactan (molecular weight greater than the 20,000 dalton form), or degradative products (molecular weight below the 20,000 dalton form) can be used. Purified arabinogalactan has a single peak of 20,000 daltons by gel filtration, and a ratio of galactose to arabinose of 5 to 1 as determined by the alditol acetate method. It binds the asialoglycoprotein receptor on hepatocytes [Josephson Groman et al. Mag. Res. Imag. (1990) 8: 637–646]. It has been shown that L-arabinose, and D-galactose interact with the asialoglycoprotein receptor while, for example, common monosaccharides like glucose or mannose do not [Lee, Haekyung, Kelm, et al., Biol. Chem., Hoppe-Seyler (1988) 369: 705–714]. It has also been shown that an underivatized 4-hydroxy group on galactose and the clustering of suitable sugars, as is displayed by highly branched polysaccharides like arabinogalactan, are important factors in binding the asialoglycoprotein receptor. Given these requirements, and based on the above composition and structure, arabinogalactan is distinguishable from other polysaccharides including dextrans, starches, celluloses, inulins, 1–4 linked galactan and gum arabic. Though chemically distinguishable from arabinogalactan, gum arabic is another polysaccharide which like arabinogalactan interacts with the asialoglycoprotein receptor.

The present invention provides for conjugates of arabinogalactan with the therapeutic agents such as ARA-AMP or WR2721. The present invention also provides derivatives of arabinogalactan which interact with the asialoglycoprotein receptor. When an arabinogalactan derivative is recognized by the asialoglycoprotein receptor, a therapeutic agent can be targeted into the cells possessing that receptor, chiefly the hepatocytes. Asialoglycoprotein receptors are dramatically reduced in primary hepatocellular cancers, and totally absent in secondary cancers to the liver, but are found in high concentration on normal hepatocytes [Josephson, Groman et al., Mag. Res. Imag. (1990) 8:637–646]. Hepatocytes are the predominant cell possessing this receptor, and endocytose a large proportion of injected radiolabelled asialoglycoproteins [Hubbard, Wilson et. al., J. Cell Biol. (1979) 83:47–64]. However, asialoglycoprotein receptors have been detected on Kupffer cells [Lee, Haekyung, et al. Biol. Chem. Hoppe-Seyler (1988) 369: 705–714], bone marrow cells [Samoloski and Daynes, Proc. Nat. Acad. Sci. (1985) 82:2508–2512] and rat testis [Abullah and Kierszenbaum, J. Cell Biol. (1989) 108: 367–375]. Useful amounts of a therapeutic agent may be targeted to any asialoglycoprotein receptor positive cell. Similarly any receptor positive cell, including stem cells, may be protected with a receptor targeted radioprotective agent based on arabinogalactan.

ARA-AMP is an antiviral therapeutic agent that has been evaluated in the treatment of hepatitis B, though its use is associated with serious neurological side effects [Lok, A. S., Wilson, L. A. et al., J. Antimicrob. Chemother. (1984) 14: 93–9; Hoffnagel, J. H. et al., J. Hepatol. (1986) 3: S73–80]. ARA-AMP conjugated to arabinogalactan, and targeted to asialoglycoprotein receptor possessing cells where viral replication is ongoing (hepatocytes), is expected to reduce unwanted side effects by reducing the concentration of the drug in the central nervous system and increasing the concentration of the drug in the organ of viral replication. ARA-AMP has been coupled to a glycoprotein recognized by the asialoglycoprotein receptor [US 4794170]. Other antiviral therapeutic agents which may be used for this purpose include acyclovir and Ara-A.

A second type of anti-viral agent that can be targeted with the teachings of the invention are antibodies. In this context antibodies may include polyclonal antibodies, monoclonal antibodies or antibody fragments. The natural occurrence of antibodies in serum reflect past exposure to a virus but may have little or no protective activity because viral replication occurs within the cytoplasm of cells [I. M. Roitt, "Essential Immunology," Blackwell Scientific London, (1991), p. 28]. In particular hepatitis B virus replication occurs within the hepatocytes of the liver and antibodies to viral antigens cannot directly bind the virus during this replication. If an antibody to a hepatitis B viral protein is conjugated to arabinogalactan, it will be targeted via the asialoglycoprotein receptor to the cytoplasm of hepatocytes. Within the cytoplasm the antiviral antibody will bind replicating hepatitis B virus and become an effective therapeutic agent.

Some of the arabinogalactan derivatives described have no known pharmacological activity, other than their ability to bind the receptor, but provide a substrate for attaching therapeutic agents, e.g., attachment to the amino, carboxyl, sulfhydryl, phosphoryl or other functional groups of the derivative. The resulting conjugate will target the therapeutic agent to cells possessing the asialoglycoprotein receptor, principally the hepatocytes of the liver. The carboxyl groups afforded by the succinyl-arabinogalactan, glutaryl-arabinogalactan and DTPA-arabinogalactan conjugates (Examples 10–12) can be used to attach molecules through the use of carbonimides or other agents. The amino groups afforded by the arabinogalactan hydrazide (Example 3) or poly-L-lysine arabinogalactan (Examples 6, 8) can also be used to attach therapeutic agents by a variety of reactions. The strong positive charge of poly-L-lysine can cause some agents such as negatively charged nucleic acids to adhere by ionic exchange forces [Wu, G. Y. and Wu, C. H., J. Biol Chem. (1987) 262: 4429–2232]. A preferred embodiment of this invention is a composition comprising arabinogalactan and poly-L-lysine, wherein the intended use is as a carrier for genes or antisense oligonucleotides used in parenteral administration [Degols, G., Leonetti, J. P., Gagnor, C., Lemaitre, M., Lebleu, B., Nucleic Acids Res (1989) 17: 9341– 50]. In addition to poly-L-Lysine, other polymeric molecules, such as dextrin, dextran, or albumin may be coupled to arabinogalactan.

In another embodiment, galactose oxidase treatment of arabinogalactan can be used to create aldehyde groups. The aldehyde groups can be reacted with diamino compounds (e.g. ethylenediamine), to form a Schiff base, followed by reduction with sodium borohydride. The resulting amino derivative of arabinogalactan can then be used for the attachment of therapeutic agents.

Similarly WR2721 has been the subject of recent clinical studies to ascertain whether it can be used to protect the normal cells of cancer patients during radiotherapy [Kligerman, M. M., Liu, T., Liu, Y., He, S., Zhang, Z., 7th International Conference on Chemical Modifiers of Cancer Treatment (1991), Clearwater, FA 338– 340] or chemotherapy [Schein, P. S, International Conference on Chemical Modifiers of Cancer Treatment (1991), Clearwater, FA 341–342]. The utility of WR2721 as a chemoprotectant has been objected to based on the lack of evidence that it selectively protects normal cells; i.e. it may protect normal and cancer cells from radiation [The Pink Sheet, Feb 3, 1992, 54, #5]. The attachment of WR2721 to arabinogalactan will overcome this shortcoming, directing the agent to cells possessing the asialoglycoprotein receptors. The radioprotective activity of WR2721 will be targeted to normal cells since the asialoglycoprotein receptor is found chiefly on non-cancerous hepatocytes, see above.

Free radical scavengers other than WR2721 can be attached to arabinogalactan, and targeted to receptor bearing cells. These scavengers include melanins [Hill, H. Z., Huselton, C., Pilas, B., Hill, G. J.; Pigment Cell Res (1987) 1: 81–6], Trolox [Wu, T. W., Hashimoto, N., Au, J. X., Wu, J., Mickle, D. A., Carey, D., Hepatology (1991) 13: 575– 80], cysteamine derivatives [Schor, N. F., Siuda, J. F., Lomis, T. J., Cheng, B., Biochem J. (1990) 267: 291–6], cationic aminothiols generally, glutathiols, and vitamin E derivatives.

After synthesis, the interaction of the arabinogalactan derivative with the asialoglycoprotein receptor can be determined in vivo. The ability of a derivative to interact with the asialoglycoprotein receptor is assessed by its ability to block the clearance of a substance recognized to interact with the asialoglycoprotein receptor based on earlier work. An arabinogalactan coated superparamagnetic iron oxide colloid interacts with this receptor and a quantitative assay for its clearance has been described below. In the absence of a blocking agent, the arabinogalactan coated superparamagnetic iron oxide is rapidly cleared via the asialoglycoprotein receptor with a blood half-life of 2.8 minutes. The interaction of free arabinogalactan with the asialoglycoprotein receptor effects an increase in blood half-life of this substance, providing a basis for evaluating the blocking ability of arabinogalactan derivatives.

To obtain the blood half-life a Sprague-Dawley rat (200–300 grams) is anesthetized (100 mg/kg of Inactin) and injected with a defined dose of a blocking agent, followed by an arabinogalactan coated superparamagnetic iron oxide at 40 umoles Fe/kg. Blood is withdrawn and 1/T1, the spin-spin relaxation rate, determined. The enhancement in 1/T1 is directly proportional to the concentration of superparamagnetic iron oxide, and from changes in 1/T1 the blood half-life is determined as described [Josephson et al. Mag Res. Imag. (1990) 8: 637–646].

Table 1 indicates that arabinogalactan can tolerate a substantial degree of modification produced by many different types of reactions, without losing its activity as a blocking agent (receptor binding activity). With antibodies and enzymes, covalent modification especially high levels of covalent modification, generally decreases or destroys biological function. Thus it is surprising that arabinogalactan tolerates random modification with excellent retention of its receptor-recognizing biological activity. In fact two derivatives tested, the phosphoryl arabinogalactan and succinyl-arabinogalactan, were more potent as blocking agents than the parent arabinogalactan. The basis for this highly surprising improved reactivity is unknown. In contrast, lactose, a disaccharide-containing galactose, is substantially less active a blocker than arabinogalactan.

The ability of a derivatization procedure to damage the binding affinity of arabinogalactan for the asialoglycoprotein receptor is shown by example 18. The acetate derivative has greater than 5 milli-equivalents of acetate per gram of arabinogalactan acetate and exhibited substantially reduced blocking activity.

If an arabinogalactan conjugate is inactive in the blocking assay, i.e., does not prolong blood half-life, conditions used in conjugate synthesis can be adjusted to achieve a lower degree of modification. Alternatively, the modification strategy employed may be dropped altogether and a different procedure employed.

TABLE 1

Interactions of arabinogalactan derivatives with the asialoglycoprotein receptor

| Agent | Dose Blocking Agent (mg/kg) | Half-life (min) |
|---|---|---|
| None | none | 2.8 |
| lactose | 300 | 8.0 |
| arabinogalactan | 150 | 33.2 |
| phosphoryl-arabinogalactan (Example 9) | 150 | 51.0 |
| succinyl arabinogalactan (Example 11) | 150 | 213 |
| arabinogalactan-AMP (Example 4) | 150 | >100 |
| arabinogalactan-WR2721 (Example 15) | 150 | 86 |
| arabinogalactan acetate (Example 18) | 150 | 7.3 |
| arabinogalactan propionate (Example 19) | 150 | 40.8 |

The examples below demonstrate that arabinogalactan can be modified by the addition of phosphoryl, sulfhydryl, amino, carboxyl, halo, or acylimidazol groups, with receptor binding activity being unaffected. The initial modification is performed on the hydroxyl groups on the arabinogalactan. The derivatives can be used to prepare conjugates with therapeutic agents, as for example arabinogalactan-WR2721 or arabinogalactan-AMP (Table 1). In some cases we describe the preparation of amino or carboxy arabinogalactan derivatives with no known therapeutic activity. These derivatives can be used to attach a wide range of drugs or ligands to the amino or carboxy groups of derivatized arabinogalactan, with generally known crosslinking and conjugation chemistries. These derivatives can also be used to attach macromolecules like genes, proteins, antibodies and enzymes to arabinogalactan. A recent compendium of applicable reactions is S. W. Wong, "Chemistry of Protein Conjugation and Cross-linking," CRC Press Boca Raton, 1991). Reagents used to couple proteins to solid phase amino or carboxyl groups can also be used after minor modifications (see I Chibata, "Immobilized Enzymes," Halstead Press New York 1978). Some examples of therapeutic agents that can be conjugated to arabinogalactan to provide useful pharmaceutical agents are listed in Table 2.

TABLE 2

Therapeutic agents that have been or might be attached to arabinogalactan or arabinogalactan derivatives

| Agent | Class | Reference |
|---|---|---|
| Ara-AMP | antiviral activity | Example 5 |
| WR2721 | chemo- and radioprotective activity | Example 14 |
| Pepstatin | anti-inflammatory activity | Example 17 |
| DNA | gene therapy | Examples 6, 8 |
| Antisense nucleic acid | antiviral activity | Examples 6, 8 |
| Antibody to hepatitis | antiviral activity | |
| Steroid anti-inflammatory activity | | |
| Superoxide dismutase anti-inflammatory activity | | |

EXAMPLES

Example 1: Bromination of arabinogalactan

The arabinogalactan (AG) used is from the Western Larch and chromatographs produce a single peak of about 20,000 daltons by size exclusion chromatography.

Ten grams of arabinogalactan are dissolved in 35 ml of a 7.1% (w/v) solution of $Zn(BF_4)_2$. Fifty ml of epibromohydrin is added and the solution stirred for 90 minutes at 100° C. The bromo-arabinogalactan is precipitated in 150 ml cold (4° C.) acetone, redissolved in water, and precipitated in 150 ml cold ethanol. Analysis of the product for bromine showed 0.7 milliequivalents bromide per gram product.

Example 2: Treatment of arabinogalactan with sodium borohydride

Ten grams sodium borohydride is added to 3,500 grams of a 28.6% (w/w) solution of arabinogalactan. The mixture is stirred overnight, and then dialyzed for six days against 35 liters of water (changing the water daily) using 3,500 dalton cut-off dialysis tubing to remove unreacted $NaBH_4$.

The 3-methyl-2-benzothiazolone hydrazone test for aldehyde is used to compare the aldehyde content of the arabinogalactan starting material to sodium borohydride reduced arabinogalactan. Arabinogalactan showed the blue dye formation characteristic of aldehyde, reduced arabinogalactan produced no dye, indicating essentially complete reduction.

Example 3: Hydrazino-arabinogalactan

Ten grams of reduced arabinogalactan (Example 2) is dissolved in 35 ml of a 7.1% (w/v) aqueous solution of $Zn(BF_4)_2$. Fifty ml of epibromohydrin is added and the solution stirred for 90 minutes at 100° C. The brominated arabinogalactan is precipitated in 150 ml cold (4° C.) acetone, redissolved in water, and precipitated in 150 ml cold ethanol. Five grams of this brominated arabinogalactan product is dissolved in 15 ml of 0.3M aqueous borate, pH 8. Ten grams hydrazine is added and the mixture is stirred for 24 hours at room temperature. The hydrazido-arabinogalactan is precipitated in 150 ml cold (4° C.) acetone, redissolved in water and precipitated in 150 ml cold ethanol. The product hydrazide content is analyzed by acid-base titration and showed 0.25 milliequivalents hydrazide per gram of product.

Example 45 Arabinogalactan conjugated to adenosine 5' monophosphate (AMP)

One gram (2.9 mmoles) of adenosine 5'-monophosphate (AMP) is dissolved in 20 ml water with the addition of sodium bicarbonate powder. Arabinogalactan-hydrazide (0.6 g, example 2) is added and the pH adjusted to 7.5 with sodium hydroxide. One gram (5.2 mmoles) of 1-ethyl-3, 4dimethylaminopropyl) carbodiimide is added and the reaction maintained at room temperature for 64 hours. The product is purified by ultrafiltration using an Amicon YM3 ultrafilter, further purified by precipitation from ethanol. A yield of 323 mg of product was obtained. The product was analyzed by cation exchange chromatography (Rainin Synchropak, strong cation exchange So 300 A, 25×0.5 cm column) using a buffer of 0.1 mM, pH 7.0 phosphate buffer at flow rate 0.5 ml/min). A single broad peak at 5.7 minutes with no evidence for underivatized AMP (retention time 6.3 minutes) was observed. The number of AMP molecules per gram of AGAMP product, based on the comparison of HPLC area under the curve monitoring at 260 nm is 0.24, indicating approximately a 95% conversion of available hydrazide groups. The UV/VIS spectrum of the AG-AMP product is virtually identical to underivatized AMP. The analysis of product by size exclusion (Amicon Cellufine GC200M) chromatography shows a molecular weight approximately equivalent to underivatized arabinogalactan, about 20,000 daltons.

The activity of AG-AMP was evaluated in the animal model as described above. 150 mg/kg of this substance was an effective blocker of the superparamagnetic iron-oxide colloid, extending the half-life of the colloid to greater than 100 minutes (Table 1).

Example 5: Arabinogalactan conjugated to adenine arabinoside 5' monophosphate (ARA-AMP)

One gram (2.9 mmoles) of adenine arabinoside 5'-monophosphate (ARA-AMP) is dissolved in 20 ml water with the addition of sodium bicarbonate powder. 0.6 grams of arabinogalactan-hydrazide (Example 2 above) is then added and the pH adjusted to 7.5 with the addition of sodium hydroxide. One gram (5.2 mg) of 1-ethyl-3,4-dimethylaminopropyl) carbodiimide is added and the reaction maintained at room temperature for 64 hours. The product is purified by ultrafiltration using an Amicon YM3 ultrafilter, and then further purified by precipitation from ethanol and dried, yielding 280 mg of product. As with AG-AMP (Example 3), the strong cation exchange chromatography showed a single broad peak centered at 5.7 minutes and no measurable residual unreacted ARA-AMP. The UV/VIS spectrum of AG-ARAAMP was virtually identical to an ARA-AMP standard. Based on the area under the curve at an optical density of 260 nanometers and in comparison with an AMP standard, which is assumed to have the same extinction coefficient as ARA-AMP, the product has 0.124 milliequivalents of ARA-AMP per gram.

Example 6: Poly(L)lysyl-arabinogalactan (prepared by reductive amination)

Poly(L) lysine hydrochloride (1,000–4,000 daltons, 0.5 grams) is dissolved in 2 ml borate buffer (0.2M) and the pH adjusted to 9.0 with sodium hydroxide. 100 mg arabinogalactan and 50 mg sodium cyanoborohydride is added. and the reaction heated for 24 hours at 50° C. The product mixture is purified using an Amicon YM3 ultrafilter. The retentate containing the polylysine-arabinogalactan conjugate showed a positive ninhydrin test for amine and positive anthrone test for polysaccharide. The yield was 30 mg. Size exclusion high performance liquid chromatography (Amicon Cellufine GC200M) showed a product having a molecular weight approximately equal to the sum of molecular weights of arabinogalactan and poly(L) lysine or about 25,000 daltons.

Example 7: Acylimidazole-arabinogalactan

Three grams of anhydrous arabinogalactan is suspended in 5 ml of anhydrous peroxide free dioxane. While stirring, 1.62 gm (10mmole) of N,N'-carbonyl diimidazole, dissolved in 10 ml of dioxane, is added in a single portion. After stirring for 20 minutes the acylimidazol-arabinogalactan is collected by filtration (medium frit). The product is washed with 25 ml of dioxane and refiltered. A second dioxane titration is performed. The product is next titrated with 25 ml of apf-diethyl ether and then vacuum dried. Yield is 2.9 gm.

Example 8: Poly(L)lysine-arabinogalactan (prepared from acylimidazole-arabinogalactan)

One gram of acylimidazole-arabinogalactan (Example 7) and 0.2 grams poly(L) lysine (1,000–4,000 daltons) is dissolved in 5 ml of 0.2M borate buffer and the pH adjusted to 8.6 with sodium hydroxide. The reaction is allowed to proceed for 24 hours at 5° C. The product is isolated first by precipitation in ethanol, and then purified using an Amicon YM10 ultrafilter. The retentate shows a positive test for amine and carbohydrate using the ninhydrin and anthrone tests, respectively, while the final filtrate is negative for amine. The yield is 310 mg.

The product poly(L) lysyl-arabinogalactan is analyzed by cation exchange chromatography HPLC (Rainin Synchropak strong cation exchange resin, So 300A, 25×0.5 cm), using pH 5.5, 25 mM phosphate buffer at a 1 ml/min flow rate. The product, arabinogalactan-polylysine, elutes with a retention time of 3.9 minutes whereas unconjugated polylysine elutes with a retention time of 9.3 minutes. Poly(L) lysine bound to arabinogalactan is verified by its UV spectrum.

Example 9: Phosphoryl-arabinogalactan

Two grams of arabinogalactan are dissolved in 20 ml formamide and 4 ml triethylamine. Ten grams polyphosphoric acid are added and the reaction stirred for 16 hours. The product is brought to pH 9 with 45% NaOH and ultrafiltered in a 50 ml stirred cell with a 3,000 molecular weight cutoff membrane (Amicon), bringing the volume from 50 ml to 10 ml twice. The ultrafiltered product is precipitated into 500 ml cold acetone (4° C.), redissolved, and precipitated in 500 ml cold ethanol. The product showed 0.21 milli-equivalents of phosphate per gram of product both by acid base titration and by colorimetric quantitation of inorganic phosphate (inorganic phosphorus kit, Sigma Chemical, St. Louis, Mo.) following trifluoroacetic acid hydrolysis (2M acid for 1 hour at 120° C.).

The activity of phosphorylated arabinogalactan was evaluated in the animal model as described above. 150 mg/kg of this substance was an effective blocker of the superparamagnetic iron-oxide colloid, extending the half-life of the colloid to greater than 51 minutes (Table 1).

Example 10: Treatment of arabinogalactan with galactose oxidase (GO)

Ten grams of arabinogalactan is dissolved to a total volume of about 50 ml in 0.1M potassium phosphate buffer, pH=6.0. To the resultant solution is added 225 units of galactose oxidase dissolved in about 2 ml of the same buffer. The oxidation is allowed to proceed for 24 hours at room temperature. The $H_2O_2$ content is found to be about 3 mg/ml, as measured by peroxide test strips. A second addition of 225 units of GO is made to the reaction mixture. After another 24 hour reaction period the peroxide content is found to be unchanged from the result of the first GO treatment at about 3 mg/ml. Twenty milligrams of catalase (dry solid) is added to decompose the peroxide. After standing at room temperature overnight the contents of the flask are found to be free of peroxide.

Product Purification. Ten grams of mixed bed resin, MB-1 is added to the flask. After stirring for 30 minutes the solution is decanted into and passed through a short column containing an additional 5 grams of MB-1 resin. The pH neutral solution is found to be free of any protein amines by reaction with ninhydrin. The product is isolated by precipitation from 5° C. cooled absolute ethanol. The precipitate is collected by filtration. The aldehyde content of this product is found to be between 3 and 5 times greater than the aldehyde content of native arabinogalactan. Yield is 10 grams.

Determination of the Number of Aldehyde Groups: The 3-methyl- 2-benzothiazolone hydrazone test for aldehyde was used to compare arabinogalactan starting material to polyaldehydic arabinogalactan. Based on absorbance measured at 670 nm, this poly-aldehydic arabinogalactan has 0.34 milliequivalents aldehyde per gram of arabinogalactan.

Example 11: Succinyl-arabinogalactan

Purified arabinogalactan (16.0 g, 0.70 mmol) and succinyl anhydride (10.0 g, 100 mmol) were dissolved in DMSO (200 ml) at 60° C. After 1.0 hour, the clear, light yellow solution was cooled to ambient temperature and allowed to stir for an additional 48 h. The DMSO solution was added to $H_2O$ (200 ml), filtered on an Amicon YM3 ultrafiltration membrane and washed with $H_2O$ (3 times with 250 ml). The solution remaining on the membrane was frozen and lyophilized. Yield of white powder: 20.6 g. IR (KBr): 1732 $cm^{-1}$ (C=O). Titration of an aqueous solution of the conjugate with 0.01N NaOH indicated the presence of 1.96 milli-equivalents succinate per gram of succinyl-arabinogalactan.

The activity of succinyl-arabinogalactan is evaluated in the animal model as described above. 150 mg/kg of this substance was an effective blocker of the superparamagnetic iron-oxide colloid, extending the half-life of the colloid to 213 minutes (Table 1).

Example 12: DTPA-arabinogalactan

Purified arabinogalactan (20.0 g, 0.87 mmol) and the dianhydride of diethylenetriaminepentaacetic acid (DTPA) (2.15 g, 6.02 mmol) were dissolved in dimethylsulfoxide (DMSO, 200 ml) at 60° C. After 0.5 hour, the clear solution was added to $H_2O$ (ca. 500 ml) at 15° C. The solution was filtered on an Amicon YM3 and YM1 ultrafiltration membranes (5,000 and 1,000 dalton cutoff, respectively) and washed with $H_2O$ (2×400 ml). The solution (70 ml) remaining on the membrane was frozen and lyophilized. Yield of white powder was 18.8 g. The IR showed a band at 1734 $cm^{-1}$ (C=O). Titration of an aqueous solution of the conjugate with 0.010 N NaOH indicated the presence of 0.117 milliequivalents DTPA per gram DTPA-arabinogalactan.

Example 13: Glutaryl-arabinogalactan

Purified arabinogalactan (20.0 g, 0.87 mmol) and glutaric anhydride (5.00 grams, 44 mmol) were dissolved in DMSO (200 ml) at 60° C. The reaction mixture was cooled to ambient temperature and allowed to react for 16 hours. The DMSO solution was added to $H_2O$ (200 ml), filtered on an Amicon YM3 ultrafiltration membrane and washed with $H_2O$ (2 times 300 ml). The solution remaining on the membrane was frozen and lyophilized. Yield of white powder: 18.5 g (lot number 2127–179). IR (KBr): 1726 $cm^{-1}$ (C=O).

Example 14: 8–2-(3-aminopropylamino) ethyl-thiophosphate-dextran-arabinogalactan from thiophosphorylated dextran Polythiophosphorylation of dextran. Ten grams of dextran is suspended in 60 ml of anhydrous pyridine. The suspension is cooled in an ice water bath. To the cooled suspension is added dropwise with stirring 10 ml (98.4 mmoles) of thiophosphoryl chloride. Once the addition is complete the reaction mixture is allowed to warm to room temperature with constant stirring. The reaction flask is then immersed in an oil bath and heated for 16 hours at 40° C.

The slightly yellow colored reaction mixture is cooled in an ice bath. Once cooled, water is added slowly dropwise while the reaction suspension is vigorously stirred. After about 10 ml of water has been added to the reaction mixture a solution of 1N NaOH is added until a pH of 9.5 is reached. The solution is then evaporated at room temperature to an oil. The residue is mixed with 20 ml of water, which results in a clear homogeneous solution. This solution is added dropwise to 200 ml of 0° C. ethanol which is vigorously stirred. The resulting white precipitate is collected on a coarse fritted funnel and dried under vacuum.

Titration with 0.5M hydrochloric acid indicates that 1 mmole of thiophosphate is incorporated per gram of polysaccharide.

Synthesis of 2-(3-aminopropylamino)ethyl bromide, dihydrobromide. Twenty three and six-tenths grams (200 mmole) of ice cold 2-(w-aminopropylamino) ethanol is added portionwise to 200 ml of ice cold 48–52% hydrobromic acid. After stirring for 1 hour the reaction mixture is heated to reflux for 16–20 hours. The reaction mixture is vacuum dried to a reddish colored oil. The oil is titrated with 300 ml of acetone and left under refrigeration for 4 hours. The mother liquor of acetone is decanted away from the gummy residue. The residue is dissolved with 75 ml of water and the resulting solution is added to 600 ml of cold acetone. The crystalline precipitate is collected and then dissolved in boiling methanol. The resulting methanol solution is added to a 50% mixture of ethyl ether and acetone (400 ml). After cooling the mixture overnight the pure white crystals are collected and vacuum dried. The melting point of the product is 205–206° C., as reported [Piper, J. R., et.al. (1969), J. Med. Chem 12: 236–243].

Reaction of polythiophosphorylated dextran with 2-(w-aminopropylamino) ethyl bromide to form S-2-(3-aminopropylamino) ethyl-thiophosphate-dextran. Five mmoles of polythiophosphorylated dextran, sodium salt, is dissolved in 10 ml of water. To the above solution is added 5.5 mmoles of 2-(3-aminopropylamino) ethyl bromide dihydrobromide dissolved in 10 mls of water. The clear solution is stirred for four hours at room temperature. The resulting turbid solution is added dropwise to rapidly stirred 0° C. ethanol. The resulting precipitate is collected by filtration. The product is washed with twice with 25 ml portions of warm (40°–50° C.) ethanol and vacuum dried.

The extent of thioalkylation is determined by a colorimetric analysis with ninhydrin.

Reaction of S-2-(3 aminopropylamino) ethyl-thiophosphate-dextran with Arabinogalactan-acylimidazole S-2-(3 aminopropylamino) ethyl-thiophosphate-dextran is reacted with arabinogalactan-acylimidazole (Example 7) at 4° C. for 16 hours. The product is isolated and purified by ultrafiltration using a YM10 filtration membrane.

Example 15: Arabinogalactan-WR2721 from brominated arabinogalactan

Reduced arabinogalactan is brominated as described in Example 3. 2 grams of this brominated arabinogalactan is added to 1 gram of WR2721 in 10 ml of 0.2M borate and the pH adjusted to 8.0. The mixture is stirred for 16 hours at room temperature. Arabinogalactan-WR2721 is purified by Amicon YM3 ultrafiltration, then precipitated in acetone and redissolved in water. Finally it is precipitated in ethanol and dried. The final product is dissolved in 0.1N HCl and titrated with 0.1N NaOH. Using WR2721 as a reference for the titration, the arabinogalactan-WR2721 final product was shown to have 0.66 milli-equivalents of WR2721 per gram of product. The product analyzed by size exclusion chromatography (Amicon Cellufine GC200M) shows the major component has a molecular weight of about 25,000 daltons.

The activity of arabinogalactan-WR2721 was evaluated in the animal model as described above. Injection of 150 mg/kg of this substance was an effective blocker of the superparamagnetic iron-oxide colloid clearance, extending the half-life of the colloid to 86 minutes (Table 1).

Example 16: Arabinogalactan-WR2721 from phosphorylated arabinogalactan

Arabinogalactan-phosphate (8 grams, example 9), 1.2 grams 1-ethyl -(3,4-dimethylaminopropyl)carbodiimide, and 1 gram of WR2721 are mixed together in 20 ml of water. The pH is adjusted to 7.5 with the addition of sodium hydroxide, and the mixture allowed to stand in the dark at room temperature for approximately 64 hours. The product, WR2721 linked to arabinogalactan through its primary amine esterified to the phosphate on arabinogalactan-phosphate, is purified by ultrafiltration (5 times 10 ml) using a YM3 (3000 daltons cutoff) and then freeze dried. The yield is 0.63 grams of white crystalline powder.

Characterization i. Molecular weight. Size exclusion chromatography (Amicon Cellufine GC200M) showed a single peak centered at 22 minutes, similar to that observed for arabinogalactanphosphate starting material. No evidence was seen of low molecular weight impurities.

ii. Analysis of sulfhydryl content. The product phosphate linked arabinogalactan-WR2721 is first hydrolyzed in 2M trifluoroacetic acid for 1 hour at 120° C. After neutralization, the sulfhydryl concentration is measured by a colorimetric test using 5,5' bisdithio 2-nitrobenzoic acid. The amount of WR2721 on arabinogalactan was determined to be 0.063 milli-equivalents per gram of product.

iii. Enzyme catalyzed hydrolysis. Both alkaline phosphatase (Biozyme Code ALPI-12G) at pH 8.0 and acid phosphatase (EC3.1.3.2, from potato) at pH 4.8 were found to rapidly hydrolyze the phosphothioate ester and thus unblock the thiol. The rate of hydrolysis by the acid phosphatase was 0.1 micro-equivalents phosphate/minute at 27° C., a rate which is close to that expected from the hydrolysis of p-nitrophenyl phosphate.

Example 17: Arabinogalactan-pepstatin

Pepstatin can be conjugated to amino-arabinogalactan (2% amine by weight polysaccharide) through a N-hydroxy succinimide ester [Furuno, K., et.al. (1983) J. Biochem 93: 249]. Arabinogalactan with a primary amine is prepared according to Example 2 (arabinogalactan-hydrazide) or example 5 or 7 (polylysine-arabinogalactan). Dissolve pepstatin A (250 mg) in 1 ml of dimethylformamide. Then add 50 mg 1-ethyl-3(3-dimethyl-aminopropyl)carbodiimide and 30 mg of N-hydroxy succinimide. After the reaction has proceeded at room temperature for 2 hours, add the mixture dropwise to 30 ml of 0.1M sodium bicarbonate containing 100 mg of amino-arabinogalactan. Allow the resultant mixture is sit at room temperature for 2 h, then purify the product by ultrafiltration using a 10,000 dalton cutoff, and then by cationic exchange chromatography.

Example 18: Carboxymethyl-arabinogalactan from reaction of bromoacetic acid with arabinogalactan Five grams of arabinogalactan is dissolved in 50 ml of 4N sodium hydroxide. To this is added 10 grams of bromoacetic acid, and the mixture heated at 80° C. for three hours. The reaction is terminated by cooling to room temperature then adjusting the pH to between 7.5 and 9 using concentrated hydrochloric acid. The product is isolated and purified by G-25 column chromatography and ultrafiltration using an Amicon YM3 membrane. The extent of derivatization, ascertained by running the reaction with $^{14}C$ labeled bromoacetic acid and measuring the specific activity of the product by liquid scintillation counting, is about 5.2 milli-equivalents of carboxymethyl groups per gram of product.

The activity of this arabinogalactan acetate was evaluated in the animal model as described above. A dose of 150 mg/kg was not an effective blocker of the superparamagnetic iron-oxide colloid, extending the half-life of the colloid only to 7.3 minutes, compared to 33.2 minutes for underivatized arabinogalactan (Table 1).

Example 19: Carboxyethyl-arabinogalactan from reaction of 2-bromopropionic acid with arabinogalactan Five grams of arabinogalactan is dissolved in 50 ml of 4N sodium NaOH. To this is added 11 grams of 2-bromopropionic acid, and the mixture heated at 80° C. for three hours. The reaction is terminated by cooling to room temperature, then adjusting the pH to between 7.5 and 9 using concentrated hydrochloric acid. The product is isolated and purified by G-25 column chromatography and ultrafiltration using an Amicon YM3 membrane. The extent of derivatization, determined by acid/base titration, is about 1.3 milliequivalents propionate per gram of product.

The activity of arabinogalactan propionate was evaluated in the animal model as described above. Use of 150 mg/kg of this substance showed it to be an effective blocker in superparamagnetic iron-oxide colloid clearance assay, extending the half-life of the colloid to 40.8 minutes (Table 1).

Example 20: Arabinogalactan-WR2721 from thiophosphorylated arabinogalactan

Thiophosphorylation of arabinogalactan. Ten grams of anhydrous arabinogalactan is suspended in 50 ml of triethylphosphate. After the addition of 10.5 ml (75 millimole) of anhydrous triethyl amine, the suspension is cooled in an ice-water bath. To the cooled suspension is added dropwise with stirring 2.55 ml (25 millimole) of thiophosphoryl chloride. Once the addition is complete, the reaction mixture is warmed to room temperature and stirred for 72 hours. After this time, the arabinogalactanyl thiophosphorodichloridate product is hydrolyzed by adding 50 ml of deionized ice-water and stirring for two hours. The solvent, triethyl phosphate, is removed from the reaction mixture by extraction with 2 times with 25 ml portions of chloroform. The pH of the aqueous phase is adjusted to between 9 and 9.5 by the addition of 1N sodium hydroxide. The product is purified by ultra-filtration (50 ml to 10 ml, four cycles) using an Amicon YM3 (3000 dalton cutoff) ultrafiltration membrane. The final retentate is lyophilized to dryness.

Synthesis of 2-(3-aminopropylamino) ethyl bromide, dihydrobromide. The synthesis of 2-(3-aminopropylamino) ethyl bromide, dihydrobromide is as described in Example 14.

Reaction of polythiophosphorylated arabinogalactan with 2-(w-aminopropylamino) ethyl bromide to form S-2-(3 aminopropylamino) ethyl-thiophosphate-arabinocalactan. Five mmole of polythiophosphorylated arabinogalactan, sodium salt, is dissolved in 10 ml of water. To the above solution is added 5.5 mmole of 2-(3-aminopropylamino) ethyl bromide dihydrobromide dissolved in 10 ml of water. The clear solution is stirred for four hours at room temperature. The resulting turbid solution is added dropwise to rapidly stirred 0° C. ethanol. The resulting precipitate is collected by filtration. The product is washed twice with 25 ml portions of warm (40°–50° C.) ethanol and vacuum dried.

Thioalkylation is confirmed by a colorimetric analysis with ninhydrin.

What is claimed is:

1. A carrier capable of being attached to a therapeutic agent for the delivery thereof to a cell receptor capable of performing receptor mediated endocytosis (RME), comprising:

a composition selected from the group consisting of substantially purified arabinogalactan and degradation products thereof, such composition modified at a site by a functional residue to produce a derivative in a manner that reserves the useful affinity of the derivative for the RME cell receptor, Wherein said functional residue is selected from the group consisting of phosphoryl, sulfhydryl, amino, halo, acylimidazole, carboxyl groups and a polymeric molecule, the derivative permitting further reactions of the derivative for attaching a therapeutic agent thereto.

2. A carrier according to claim 1, wherein the site of modification of the composition is a hydroxyl group on a constituent monosaccharide.

3. A carrier according to claim 1, wherein the composition is modified at a plurality of sites.

4. A carrier according to claim 3, wherein the member of functional residues is no less than one equivalent per mole of the composition and no more than the number of hydroxyl groups on the composition per mole of the composition.

5. A carrier according to claim 1, wherein the functional residue is a polymeric molecule selected from the group consisting of dextran, dextrin, albumin and poly-L-lysine.

6. A carrier according to claim 3, wherein the functional residue is a polymeric molecule selected from the group consisting of dextran, dextrin, albumin and poly-L-lysine.

* * * * *